United States Patent [19]

Hamou

[11] Patent Number: 4,579,110
[45] Date of Patent: Apr. 1, 1986

[54] TUBULAR PESSARY AS A CONTRACEPTIVE MEANS

[76] Inventor: Jacques Hamou, 2 Chaussee de la Muette, 75016 Paris, France

[21] Appl. No.: 553,466

[22] Filed: Nov. 18, 1983

[30] Foreign Application Priority Data

Mar. 23, 1983 [WO] PCT Int'l Appl. .................. PCT/DE83/00047

[51] Int. Cl.$^4$ ................................................ A61F 5/46
[52] U.S. Cl. ..................................................... 128/130
[58] Field of Search ................ 128/130, 127, 128, 129

[56] References Cited

U.S. PATENT DOCUMENTS

| 3,757,775 | 9/1973 | Marco et al. | 128/130 |
| 3,840,005 | 10/1974 | Walker | 128/130 |
| 3,842,826 | 10/1974 | Nolan | 128/130 |
| 3,937,217 | 2/1976 | Kosonen | 128/130 |
| 4,198,966 | 4/1980 | Kaivola | 128/130 |

Primary Examiner—John D. Yasko
Attorney, Agent, or Firm—Donald D. Mon

[57] ABSTRACT

The invention relates to a tubular pessary having a contraceptive action through the obturation of the proximal uterine tube in non-surgical manner by hysteroscopy and which can easily be worn on either side.

The tubular pessary has a cylindrical, sensitive central part permitting the obturation of the uterine tube. It has a distal elastic loop, which prevents sliding back into the uterus of the device. It has a proximal elastic loop, which prevents migration of the device into the abdominal cavity and which can easily be removed through a hysteroscope.

The object of the invention is to overcome the inadequacies of the known contraceptive means.

14 Claims, 3 Drawing Figures

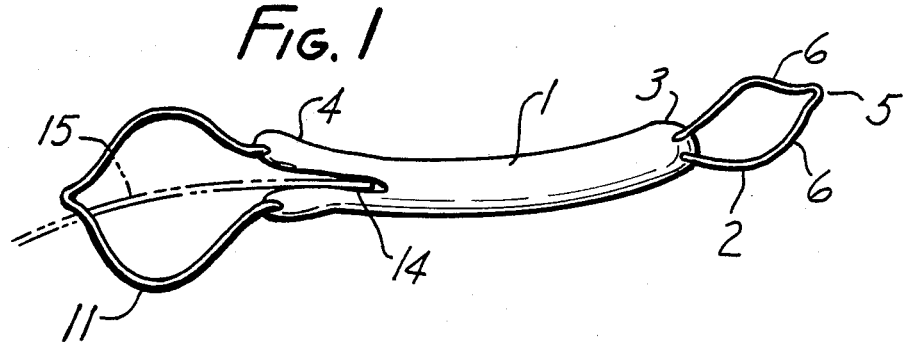
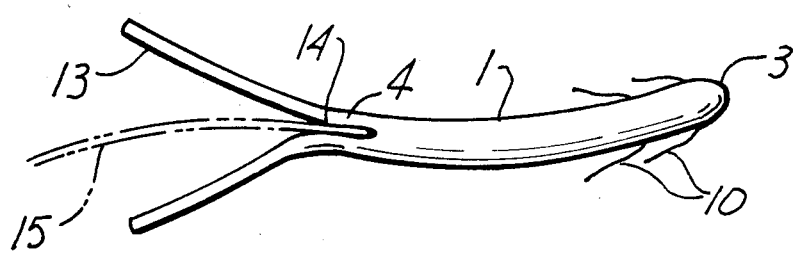
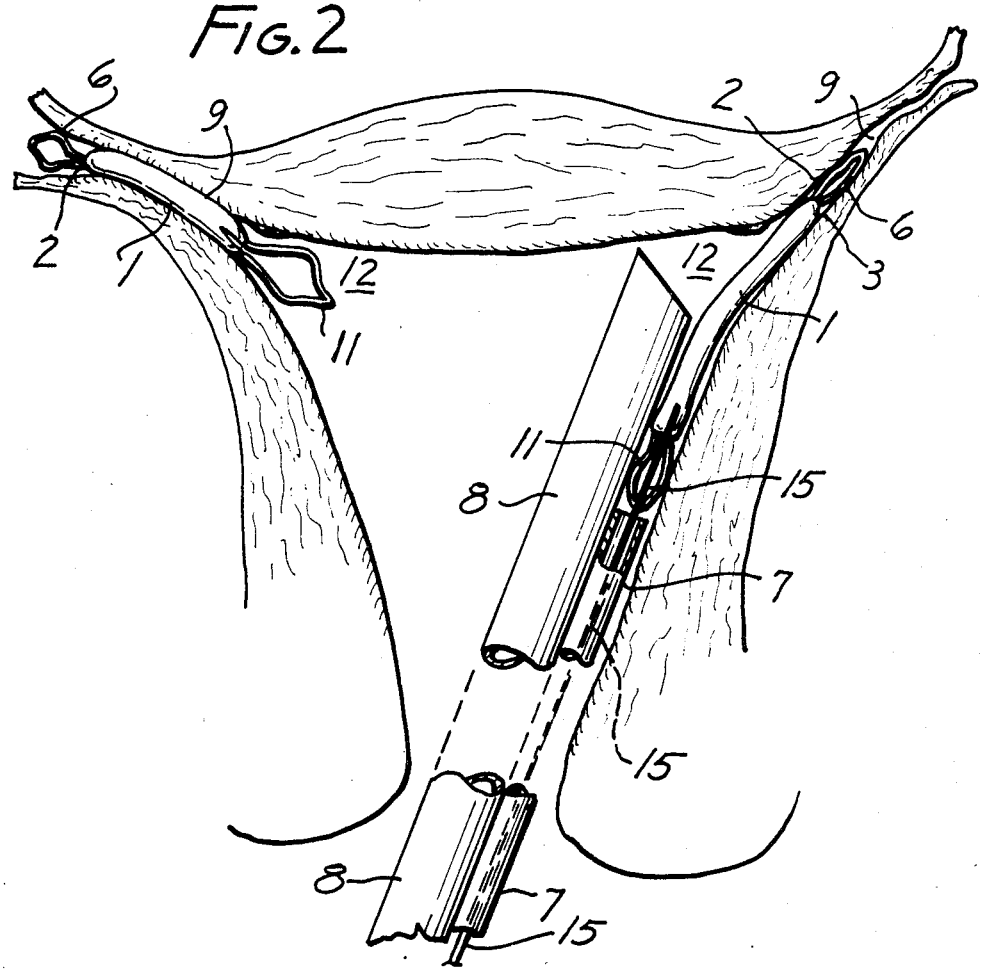

TUBULAR PESSARY AS A CONTRACEPTIVE MEANS

FIELD OF THE INVENTION

The invention relates to a tubular pessary for the fallopian tubes as a contraceptive means implanted by non-surgical hysteroscopy and which women can carry or wear on either side.

BACKGROUND OF THE INVENTION

All the known methods and devices of this type have limits, with regards to application and effectiveness.

Ideally, a contraceptive means must have a 100% efficiency, but enable unimpeded sexual intercourse, be comfortable to wear, inexpensive and in particular being removable to reverse the contraceptive effect.

Already, numerous contraceptive means are known, e.g. devices which are inserted into the vagina, condoms and the like, but these are not completely effective. Devices which are inserted into the uterus, such as IUD's have the disadvantage of causing bleeding and pain, as a result of contact in the uterus with the discharges thereof. This makes regular replacement necessary in order to physically modify the surfaces and also adapt to chemical menstruation. Contraceptive pills on a hormone base lead to the known side-effects. Sterilization by ligation of the uterine tube, resection, rings or clamps, leading to irregularity in the funnel-shaped ectasias, are also disadvantageous. Thus, these methods require surgery and it is difficult, if not impossible, to restore receptivity for normal reproduction.

Finally, means exist for closing the trumpet-shaped ectasias by injection using a hysteroscope, using a mixture of a liquid preelastomer and a catalyst injected for polymerizing the material in the uterine tube. However, this requires a special technique with a local anesthetic, requiring a pumping device for injection. There is also a possibility of failure and the increased risks, due more particularly to the instability of the injection material. Reversibility through the use of hysteroscopy is theoretically possible, but the passage of the distal outer end of the syringe having a diameter of several millimeters can injure the isthmian canal of the trumpet-shaped ectasia with a diameter below 1 mm, despite the elasticity of the elastomer.

BRIEF DESCRIPTION OF THE INVENTION

The problem of the invention is to overcome the aforementioned disadvantages of known contraceptive means and to provide a novel, non-surgical technique, which is easy to use, inexpensive and reversible.

The aim is to provide a pessary for the fallopian tubes which permits an obturation by using a hysteroscope, as is generally known in the field of gynecology, through which the device can be very easily removed, or in which a clamp is used.

BRIEF DESCRIPTION OF THE DRAWINGS

The invention is described in greater detail hereinafter relative to non-limitative embodiments and the attached drawings, in which:

FIG. 1 is a side view of a first embodiment of the tubular pessary;

FIG. 2 shows the tubular pessary of FIG. 1 in its operative position.

FIG. 3 shows another embodiment of the tubular pessary.

DETAILED DESCRIPTION OF THE INVENTION

The central part of the device preferably has a cylindrical cross-section, is soft and is made from a plastic material, such as medical nylon and which is medically inactive. It is approximately 1 cm long and has a diameter of 1 to 2 mm. However, it is also possible to use other dimensions, in order to adapt to the function and anatomy of the isthmian channel. Its distal outer end must be soft or rounded, in order to prevent any injuries in this area. The proximal area 4 can be widened, in order to adapt to the funnel shape of the entrance of the funnel-shaped ectasia.

The distal loop 2 is preferably made from surgical nylon or some other soft material, which is medically inactive. According to a preferred embodiment, the loop is oval and has a diameter of 3 to 6 mm, the distal end being formed by an acute angle or a rounded portion 3, in order to facilitate insertion. The two shown parts 6 can easily be moved towards one another in order to guide them in channel 7 of hysteroscope 8 and to move them into the isthmian channel 9. Subsequently, these parts can be spread apart again, when they are in their desired position, in order to prevent an undesired movement of device 1 in the direction of the uterus.

The diameter of this filamentary, distal loop 6 is preferably approximately half the diameter of central part 1.

According to a modified embodiment, the central part 1 can be provided with a plurality of attachments in the form of small branches 10, which point in the direction of the proximal ends, in order to prevent sliding back into the uterus, and curvatures to adapt to the surrounding area.

Preferably, the proximal loop 11 is constructed in a similar manner to the distal loop 2, the two parts 11 also being movable towards one another in channel 7 of hysteroscope 8. In the uterus 12, they move resiliently apart and prevent any migration of device 1 in the direction of the abdominal cavity. Loop 11 is used for the withdrawal of the device through the hysteroscope by means of forceps or a clamp arranged in insertion channel 7 in per se known manner.

According to a further embodiment of FIG. 3, small elastic branches 13 can be provided to prevent device 1 from migrating in the direction of the abdominal cavity. They also permit a reciprocal approximation in insertion channel 7 and can be spread apart in uterus 12 after reaching their operative position.

According to another embodiment, it is also possible to provide a blind channel 14, according to FIG. 1 or 3, in the vicinity of the proximal end 4 of device 1, in order to permit the insertion of a metal guide member 15, which is flexible and facilitates insertion and the guidance of device 1 in situ.

According to another preferred embodiment, the device can be provided with a medium which is transparent to X-rays. This can be provided either by an axial additive or through the medium being in the mass of a metallic substance. However, it can also be a chemical medium, which has a certain radiopacity.

According to another embodiment, a pharmacodynamic, physical or chemical effect can be desired, for which purpose the surface of the device is provided with chemical-medicamentous, metal coatings or invariable alloys.

As stated hereinbefore, the device is inserted by means of a hysteroscope. To this end, the tubular pessary is placed in the insertion channel 7 of the endoscope and is moved forwards by means of a metal or plastics guide wire 15 until the device has reached the end position shown in FIG. 2.

Numerous variants are possible to the embodiments described hereinbefore without passing beyond the scope of the invention.

What is claimed is:

1. A tubular pessary for reversible contraception by obturating the isthmian channel, wherein the device has a cylindrical central part made from medically inactive material, with a cross-section that forms a fluid-sealing fit with the wall of a fallopian tube said central part having a distal end and a proximal and, end outwardly springing and spreading attachments at each of said ends adapted to be compressed to fit into a hysteroscope, and to spring out to a radial distance greater than the radius of the central part, at least the attachment at said distal end being adapted to make contact with the said wall and resist removal of said pessary by peristaltic action.

2. A tubular pessary according to claim 1, wherein both attachments are constructed as an outwardly springing loop.

3. A tubular pessary according to claim 1, wherein the central part has a length of 0.5 to 1.5 cm and a diameter of 1 to 2 mm.

4. A tubular pessary according to claim 2, wherein the distal attachments form a loop which is approximately oval and has a diameter of 3 to 6 mm.

5. A tubular pessary according to claim 1, wherein the attachments at the distal end are filamentary and have a filament diameter which is no more than about half as large as the diameter of the central part.

6. A tubular pessary according to claim 1, wherein the distal end of the central part is soft or rounded.

7. A tubular pessary according to claim 1, wherein the proximal end of the central part has a diameter which is larger than that of the remainder of the central part.

8. A tubular pessary according to claim 1, wherein the proximal end of the central part has a blind channel for the insertion of a metallic, flexible guide wire for anchoring purposes.

9. A tubular pessary according to claim 1, wherein the attachments are constructed as one or more threads, which form an acute angle to the central part, facing toward said proximal end.

10. A tubular pessary according to claim 1, wherein the attachments at the proximal end are constructed as outwardly springing parts.

11. A tubular pessary according to claim 1, wherein the device includes a material which is radiopaque.

12. A tubular pessary according to claim 1, wherein the device is provided with a chemical, metallic or an alloyed medium, which is inert.

13. A tubular pessary according to claim 1, wherein the distal end of the device is constructed as a filamentary barb.

14. A method for using the tubular pessary according to claim 1, wherein the pessary, when placed in a channel of a hysteroscope is moved towards the distal end and out of the latter by means of a metal or plastic wire which forms part of the hysteroscope, and which fits into the proximal end of said pessary.

* * * * *